United States Patent

Schmid et al.

[11] Patent Number: 5,811,594
[45] Date of Patent: Sep. 22, 1998

[54] METHYL-END-CAPPED ALKYL AND/OR ALKENYL POLYGLYCOL ETHERS

[75] Inventors: Karl Schmid, Mettmann, Germany; Joaquim Bigorra Llosas, Sabadell, Spain

[73] Assignee: Henkel Kommanditgesellschaft auf Aktien, Duesseldorf, Germany

[21] Appl. No.: 793,703

[22] PCT Filed: Aug. 24, 1995

[86] PCT No.: PCT/EP95/03359

§ 371 Date: Mar. 3, 1997

§ 102(e) Date: Mar. 3, 1997

[87] PCT Pub. No.: WO96/06905

PCT Pub. Date: Mar. 7, 1996

[30] Foreign Application Priority Data

Sep. 1, 1994 [DE] Germany .......................... 44 31 158.3

[51] Int. Cl.$^6$ .................................................. C07C 41/16
[52] U.S. Cl. ..................... 568/619; 568/620; 568/613; 426/329; 435/243
[58] Field of Search ................... 568/619, 620, 568/613; 426/329; 435/243

[56] References Cited

U.S. PATENT DOCUMENTS

| | | | |
|---|---|---|---|
| 4,548,729 | 10/1985 | Schmid et al. | 252/174.12 |
| 4,587,365 | 5/1986 | Anchor | 568/619 |
| 4,624,803 | 11/1986 | Balzer et al. | 252/527 |
| 4,753,885 | 6/1988 | Dietsche et al. | 435/243 |
| 4,922,029 | 5/1990 | Birnbach et al. | 568/616 |
| 4,942,049 | 7/1990 | Schmid et al. | 426/329 |
| 4,973,423 | 11/1990 | Geke et al. | 252/174.21 |
| 5,484,553 | 1/1996 | Guth et al. | 252/351 |

FOREIGN PATENT DOCUMENTS

| | | |
|---|---|---|
| 1 338 277 | 4/1996 | Canada . |
| 0 012 052 | 6/1980 | European Pat. Off. . |
| 0 124 815 | 11/1984 | European Pat. Off. . |
| 0 161 537 | 11/1985 | European Pat. Off. . |
| 0 180 081 | 5/1986 | European Pat. Off. . |
| 0 202 638 | 11/1986 | European Pat. Off. . |
| 0 302 487 | 2/1989 | European Pat. Off. . |
| 0 303 928 | 2/1989 | European Pat. Off. . |
| 0 324 340 | 7/1989 | European Pat. Off. . |
| 0 420 802 | 4/1991 | European Pat. Off. . |
| 0 590 722 | 4/1994 | European Pat. Off. . |
| 22 43 307 | 3/1974 | Germany . |
| 37 44 525 | 12/1988 | Germany . |
| 39 28 600 | 3/1991 | Germany . |
| 42 43 643 | 8/1993 | Germany . |

OTHER PUBLICATIONS

Surfactants in Consumer Products, J Falbe (ed.), Springer–Verlag, Berlin, 1987, pp. 54 to 124.

*Primary Examiner*—Gary Geist
*Assistant Examiner*—Sreenivas Padmanabhan
*Attorney, Agent, or Firm*—Ernest G. Szoke; Wayne C. Jaeschke; Henry E. Millson, Jr.

[57] ABSTRACT

Methyl-end-capped alkyl and/or alkenyl polyglycol ethers; a process for their production by methylation of products of the addition of ethylene oxide and propylene oxide to primary alcohols; to formulations containing these substances; and to the use of the substances for the production of surface-active formulations.

20 Claims, No Drawings

METHYL-END-CAPPED ALKYL AND/OR ALKENYL POLYGLYCOL ETHERS

BACKGROUND OF THE INVENTION

This is the U.S. National Stage Application of PCT/EP95/ 03359 filed Aug. 24, 1995, now WO96/06905 published Mar. 7, 1996.

1. Field of the Invention

This invention relates to methyl-end-capped alkyl and/or alkenyl polyglycol ethers, to a process for their production by methylation of products of the addition of ethylene oxide and propylene oxide to primary alcohols, to formulations containing these substances and to the use of the substances for the production of surface-active formulations.

2. Prior Art

In a number of industrial processes, the presence of foam is extremely undesirable. For example, both in the machine washing of beer or milk bottles and in the spray cleaning of automobile panels, not only is the cleaning or degreasing effect of the surface-active formulations used an important factor, the avoidance of foam which can seriously interfere with plant functions is of equal significance—all the more so inasmuch as highly active and also high-foaming anionic surfactants are used in many cases.

The problem of controlling foam has been known for some time and, accordingly, a number of more or less convincing solutions to the problem are known from the prior art and may be divided into two groups:

- The first of these two groups comprises processes involving the addition of defoamers which, in many instances, are paraffinic hydrocarbons or silicone compounds. For the described applications, however, this is undesirable in most cases. The second group of processes involve the use of surface-active formulations which are themselves low-foaming and, in addition, may also exhibit defoaming properties. In general, these surface-active formulations are nonionic surfactants or surfactant-like systems such as, for example, fatty alcohol propylene glycol ethers or block polymers of ethylene and propylene glycol which, unfortunately, do not have sufficient biological degradability.

- End-capped fatty alcohol polyglycol ethers, so-called "mixed ethers", which are described for example by R. Piorr in Fat Sci. Technol.. 89, 106 (1987), have established themselves in the market as particularly effective low-foaming surfactants. These products are generally butyl-end-capped nonionic surfactants which are known, for example, from EP-A 0 124 815, EP-B 0 303 928, EP-B 0 324 340, EP-A 0 420 802, DE-A 39 28 600 and DE-C 42 43 643.

Methyl-end-capped methyl mixed ethers occupy a special position. They are normally prepared by reaction of the corresponding fatty alcohol polyglycol ethers with methyl halides [U.S. Pat. No. 4,587,365, BASF] or dimethyl sulfate [EP-B 0 302 487, BASF].

Thus, the use inter alia of methyl-end-terminated mixed ethers for machine bottle washing is known, for example, from EP-A 0 161 537 (BASF). The same substances are proposed as defoamers for the sugar and yeast industry in EP-B 0 180 081 (BASF). Finally, EP-B 0 202 638 (BASF) relates to liquid surfactant concentrates for highly alkaline cleaning compositions containing methyl mixed ethers, alkyl polyglucosides, adducts of maleic anhydride with unsaturated fatty acids and branched fatty acids.

The hitherto known methyl mixed ethers have always been distinctly inferior to the widely used butyl mixed ethers in regard to foaming power and, in particular, defoaming behavior. However, in view of the limited availability of butyl chloride as a suitable reagent for the $C_4$ end capping of alkyl polyglycol ethers, there has been a considerable increase in recent years in market demand for methyl mixed ethers with improved performance properties which are both simple and inexpensive to produce.

Accordingly, the problem addressed by the present invention was to provide new methyl-end-capped alkyl polyglycol ethers which would be free from the disadvantages mentioned above and which would be at least equivalent to butyl-end-capped commercial products in regard to foam, defoaming, cleaning performance and biodegradability.

DESCRIPTION OF THE INVENTION

The present invention relates to methyl-end-capped alkyl and/or alkenyl polyglycol ethers corresponding to formula (I):

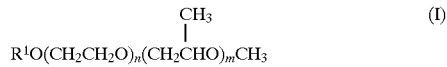

in which $R^1$ is a linear or branched alkyl and/or alkenyl group containing 6 to 22 carbon atoms, n is a number of 4 to 15 and m is a number of 1 to 10.

It has surprisingly been found that methyl mixed ethers containing a sequence of, on average, 4 to 15 moles of ethylene oxide and 1 to 2 moles of propylene oxide in the polyalkylene oxide chain have improved foam-suppressing properties in relation to known methyl mixed ethers and, in some cases, butyl mixed ethers. They are also distinguished by very low foaming, by high cleaning power and by satisfactory biological degradability.

The present invention also relates to a process for the production of methyl-end-capped alkyl and/or alkenyl polyglycol ethers corresponding to formula (I):

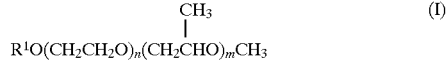

in which $R^1$ is a linear or branched alkyl and/or alkenyl group containing 6 to 22 carbon atoms, n is a number of 4 to 15 and m is a number of 1 to 10, characterized in that first an average of n moles of ethylene oxide and then m moles of propylene oxide are added in known manner to primary alcohols corresponding to formula (II):

in which $R^1$, n and m are as defined above, and the resulting polyglycol ethers are subsequuently reacted with a methylating agent.

Primary alcohols

Suitable primary alcohols are, for example, fatty alcohols corresponding to formula (II), in which $R^1$ is an alkyl and/or alkenyl group containing 8 to 18 carbon atoms.

Typical examples are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol and erucyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohols. Technical fatty alcohols containing 12 to 18 carbon atoms, for example coconut oil, palm oil, palm kernel oil or tallow fatty alcohol are preferred.

Other suitable primary alcohols are Guerbet alcohols corresponding to formula (II), in which $R^1$ is an alkyl group with 16 to 20 carbon atoms branched in the 2-position. Guerbet alcohols are normally prepared by basic condensation of fatty alcohols. A review of this subject was published by O'Lenick and Bibo in Soap, Cosm. Chem. Spec. April 52 (1987). Typical examples are 2-hexyl dodecanol and 2-octyl tetradecanol and mixtures thereof based on technical $C_{8-10}$ fatty alcohols. The last-mentioned products are distinguished by particularly high cleaning power and very good biological degradability.

Ethoxylation and PropoxYlation

The ethoxylation and propoxylation of the alcohols mentioned may be carried out in known manner at temperatures of 120° to 180° C. in the presence of basic catalysts such as, for example, sodium methylate or calcined hydrotalcite. Accordingly, the alkoxylates may have both a conventional and a narrow homolog distribution. It is again specifically pointed out that the sequence of ethoxylation and propoxylation is critical to the performance properties of the products. Methyl-end-capped mixed ethers which are to be used in accordance with the invention are obtained solely on the basis of alkyl and/or alkenyl polyglycol ethers which contain first a block of ethylene oxide units and then a small number of propylene oxide units. Mixed ethers based on alkyl and/or alkenyl polyglycol ethers containing on average 4 to 12 moles of ethylene oxide and 0.5 to 1.5 moles of propylene oxide are particularly preferred.

Methyl end capping

The methyl end capping may also be carried out in known manner, i.e. using methyl chloride or dimethyl sulfate in accordance with U.S. Pat. No. 4,587,365 or EP-B 0 302 487. It is advisable to carry out the reaction at a temperature of 60° to 120° C. and preferably at a temperature of 80° to 100° C. The end capping reaction is a Williamson's ether synthesis which can only be carried out in the presence of at least stoichiometric quantities of a strong base, for example sodium hydroxide or, more particularly, potassium hydroxide. In addition, it has proved to be of advantage to use the alkyl and/or alkenyl polyglycol ether, the base and the methylating agent in a molar ratio of 1:(1.5–2.0):(1.5–2.0).

Commercial Applications

The methyl mixed ethers according to the invention are particularly low-foaming and are distinguished by very good defoaming properties, high cleaning power and high ecotoxicological compatibility.

Surface-active formulations

Accordingly, the present invention also relates to the following surface-active formulations for example:

Formulations for machine bottle washing, more particularly for the washing of beer bottles and milk bottles, containing methyl-end-capped alkyl and/or alkenyl polyglycol ethers corresponding to formula (I).

Formulations for cleaning hard surfaces, more particularly for cleaning-in-place (CIP), containing methyl-end-capped alkyl and/or alkenyl polyglycol ethers corresponding to formula (I).

Formulations for defoaming intermediate products in sugar and yeast production containing methyl-end-capped alkyl and/or alkenyl polyglycol ethers corresponding to formula (I).

In the context of the present invention, cleaning formulations are, on the one hand, the aqueous solutions intended for direct application to the substrates to be cleaned and, on the other hand, the concentrates and optionally solid mixtures intended for the preparation of the in-use solutions. The ready-to-use solutions may be acidic to highly alkaline and are generally used at temperatures of around 20° to 90° C.

Auxiliaries and additives

The formulations according to the invention may contain other auxiliaries and additives and, in particular, other anionic, nonionic, cationic and/or amphoteric or zwitterionic surfactants.

Typical examples of anionic surfactants are alkyl benzene sulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotrigly-cerides, amide soaps, ether carboxylic acids and salts thereof, fatty acid isethionates, fatty acid sarcosinates, fatty acid taurides, acyl lactylates, alkyl oligoglucoside sulfates, protein fatty acid condensates (more particularly vegetable soya-based products) and alkyl (ether) phosphates. If the anionic surfactants contain polyglycol ether chains, they may have a conventional homolog distribution although they preferably have a narrow homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, butyl mixed ethers, alk(en)yl oligoglycosides, fatty acid N-alkyl gluc-amides, protein hydrolyzates (more particularly vegetable soya-based products), polyol fatty acid esters, sugar esters, sorbitan esters and polysorbates. If the nonionic surfactants contain polyglycol ether chains, they may have a conventional homolog distribution although they preferably have a narrow homolog distribution.

Typical examples of cationic surfactants are quaternary ammonium compounds and esterquats, more particularly quaternized fatty acid trialkanolamine ester salts.

Typical examples of amphoteric or zwitterionic surfactants are alkyl betaines, alkyl amidobetaines, aminopropionates, aminoglycinates, imidazo-linium betaines and sulfobetaines.

All the surfactants mentioned are known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive", Thieme Verlag, Stuttgart, 1978, pages 123–217.

The formulations may contain above all alkali metal orthophosphates, polymer phosphates, silicates, borates, carbonates, polyacrylates and gluconates and zeolites, layer silicates, citric acid, nitrilotriacetic acid, ethylenediamine tetraacetic acid, 1-hydroxyalkane-1,1-diphosphonic acids, ethylenediamine tetra-(methylenephosphonic acid) and phosphonoalkane polycarboxylic acids, for example phosphonobutane tricarboxylic acid, or alkali metal salts of these acids as builders and complexing agents.

In addition, highly alkaline cleaning formulations, more particularly for bottle washing, may contain considerable quantities of caustic alkali in the form of sodium and/or potassium hydroxide. If particular cleaning effects are required, the formulations may additionally contain organic solvents, for example alcohols, gasoline fractions and free alkanolamines.

Finally, the present invention relates to the use of methyl-end-capped alkyl and/or alkenyl polyglycol ethers corresponding to formula (I) for the production of surface-active formulations, more particularly low-foaming cleaning formulations and defoamers for the sugar and yeast industry, in which they may be present in quantities of 1 to 50% by weight and preferably 5 to 25% by weight, based on the formulation.

The following Examples are intended to illustrate the invention without limiting it in any way.

EXAMPLES

I General procedure for the production of mixed ethers 5.5 moles of the corresponding alkyl EO/PO adduct and 770 g (11.25 moles) of 82% by weight potassium hydroxide in flake form are introduced into a three-necked flask equipped with a KPG stirrer, an internal thermometer and a reflux condenser. The flask is evacuated and purged with nitrogen twice. After addition of 11.25 moles of methyl chloride or butyl chloride, the mixture is heated with stirring to 80° C. and left at that temperature for 8 h. Excess alkylating agent is then distilled off under a pressure of 1 bar and at a maximum bottom temperature of 200° C., nitrogen being used as the entraining gas.

The reaction mixture is then cooled to 60° C. and neutralized with 2 N sulfuric acid. Water is then added to the crude product in a quantity corresponding to its volume, the whole then being left at 50° C. until phase separation occurs. The pure product is obtained by separating off the aqueous phase.

Mixed ethers M1 to M3 produced in this way corresponded to the invention while mixed ethers M4 to M8 are intended for comparison. The particulars are set out in Table 1.

TABLE 1

Methyl and Butyl Mixed Ethers

| Ex. | R¹ | Moles EO | Moles PO | Moles EO | EC |
|---|---|---|---|---|---|
| M1 | Octyl | 4 | 1 | — | Methyl |
| M2 | Dodecyl | 7 | 1.2 | — | Methyl |
| M3 | 2-Hexyl dodecyl | 10 | 1.2 | — | Methyl |
| M4 | Octyl | — | 1 | 4 | Methyl |
| M5 | Octyl | 2 | 1 | 2 | Methyl |
| M6 | Dodecyl | — | 1.2 | 7 | Methyl |
| M7 | Dodecyl | 7 | — | — | Butyl |
| M8 | Dodecyl | 3 | 1.2 | 4 | Butyl |

Legend: EC = End capping

II. Determination of the defoaming effect

Method. 300 ml of a 1% by weight sodium hydroxide solution are heated to 20° C. and 65° C. in a double-walled 2-liter measuring cylinder. The particular foam-suppressing additive selected is then added in the quantities shown below. The liquid is circulated at a rate of 4 l/minute by a laboratory peristaltic pump, the test solution being taken in about 5 mm above the bottom of the measuring cylinder by means of a glass tube connected to a pump and being returned by free fall through a second glass tube arranged at the 2,000 ml mark.

After 30 s, 1 ml of a 1% by weight aqueous solution of tetrapropylene benzene sulfonate triethanolammonium salt (hereinafter referred to as "test foamer TF") is introduced into the liquor and the developing volume formed by liquid and foam is determined after another 30 s. More test foamer is then added at intervals of 1 minute and the foam/liquid volume formed after 30 s is determined. This step-by-step cycle of adding the test foamer and measuring the foam formed is continued until the surfactant solution has foamed to 2,000 ml in the measuring cylinder.

The results are set out in Tables 2 and 3.

TABLE 2

Defoaming Effect (20° C.)

| TF ml | M1 ml | M2 ml | M3 ml | M4 ml | M5 ml | M6 ml | M7 ml | M8 ml |
|---|---|---|---|---|---|---|---|---|
| 0 | 300 | 300 | 300 | 300 | 300 | 300 | 300 | 300 |
| 1 | 300 | 300 | 300 | 300 | 300 | 300 | 300 | 300 |
| 2 | 300 | 300 | 300 | 300 | 300 | 300 | 300 | 300 |
| 3 | 300 | 300 | 300 | 320 | 320 | 300 | 300 | 300 |
| 4 | 340 | 320 | 300 | 340 | 330 | 320 | 320 | 320 |
| 5 | 380 | 360 | 300 | 390 | 380 | 360 | 360 | 360 |
| 6 | 400 | 390 | 300 | 440 | 440 | 390 | 390 | 390 |
| 7 | 420 | 410 | 420 | 470 | 480 | 430 | 430 | 430 |
| 8 | 420 | 410 | 420 | 490 | 490 | 450 | 450 | 450 |
| 9 | 460 | 430 | 430 | 530 | 520 | 470 | 470 | 470 |
| 10 | 480 | 460 | 470 | 570 | 550 | 490 | 480 | 490 |
| 11 | 500 | 490 | 490 | 590 | 590 | 520 | 520 | 510 |
| 12 | 540 | 520 | 510 | 630 | 630 | 560 | 550 | 560 |
| 13 | 580 | 550 | 550 | 690 | 680 | 590 | 590 | 590 |
| 14 | 600 | 580 | 570 | 780 | 750 | 640 | 630 | 620 |
| 15 | 660 | 650 | 660 | 950 | 940 | 700 | 720 | 700 |
| 16 | 720 | 700 | 710 | 1150 | 1100 | 890 | 820 | 880 |
| 17 | 800 | 790 | 810 | 1700 | 1650 | 990 | 990 | 980 |
| 18 | 1000 | 950 | 990 | 2000 | 2000 | 1300 | 1290 | 1400 |
| 19 | 1300 | 1250 | 1270 | | | 2000 | 1650 | 2000 |
| 20 | 1680 | 1500 | 1530 | | | | 2000 | |
| 21 | 2000 | 2000 | 2000 | | | | | |

TABLE 3

Defoaming Effect (65° C.)

| M | ml Test Foamer to 2,000 ml |
|---|---|
| M1 | 20 |
| M2 | 20 |
| M3 | 20 |
| M4 | 15 |
| M5 | 14 |
| M6 | 15 |
| M7 | 18 |
| M8 | 15 |

We claim:

1. A process for the production of methyl-end-capped alkyl or alkenyl polyglycol ethers or mixtures thereof corresponding to formula (I):

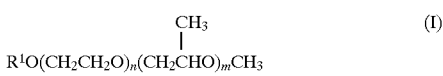

in which R¹ is a linear or branched alkyl or alkenyl group containing 6 to 22 carbon atoms, n is an average number of 4 to 15 and m is an average number of 0.5 to 1.5, comprising the steps of A) reacting at least one primary alcohol of the formula

R¹OH     (II)

wherein R¹ is as defined above, with n mols of ethylene oxide at a temperature in the range of from about 120° C. to about 180° C. in the presence of a basic catalyst, B) reacting the ethoxylated product from step A) with m mols of propylene oxide at a temperature in the range of from about 120° C. to about 180° C. in the presence of a basic catalyst; and C) reacting the product from step B) with a methylating agent at a temperature in the range of from about 60° C. to about 120° C. in the presence of an at least stoichiometric quantity of a strong base.

2. The process of claim 1 wherein in the at least one primary alcohol of formula II, R¹ is an alkyl or alkenyl group containing 8 to 18 carbon atoms.

3. The process of claim 1 wherein the at least one primary alcohol of formula II is at least one Guerbet alcohol in which R¹ is an alkyl group containing 16 to 20 carbon atoms branched in the 2-position.

4. The process of claim 1 wherein an average of from 4 to 12 mols of ethylene oxide is used in step A), and from 0.5 to 1.5 mols of propylene oxide is used in step B).

5. The process of claim 1 wherein in step C) the methylating agent is methyl chloride or dimethyl sulfate.

6. The process of claim 1 wherein step C) is carried out at a temperature in the range of from about 80° C. to about 100° C.

7. The process of claim 1 wherein in step C) the strong base is sodium hydroxide or potassium hydroxide.

8. The process of claim 1 wherein in step C) the product from step B), the strong base, and the methylating agent are present in a molar ratio of about 1:(1.5–2.0):(1.5–2.0).

9. The process of claim 1 wherein in the at least one primary alcohol of formula II R¹ is an alkyl or alkenyl group containing 8 to 18 carbon atoms or an alkyl group containing 16 to 20 carbon atoms branched in the 2-position.

10. The process of claim 9 wherein an average of from 4 to 12 mols of ethylene oxide is used in step A), and from 0.5 to 1.5 mols of propylene oxide is used in step B).

11. The process of claim 10 wherein in step C) the methylating agent is methyl chloride or dimethyl sulfate, the temperature is in the range of from about 80° C. to about 100° C., and the strong base is sodium hydroxide or potassium hydroxide.

12. The process of claim 11 wherein in step C) the product from step B), the strong base, and the methylating agent are present in a molar ratio of about 1:(1.5–2.0):(1.5–2.0).

13. In a low foaming cleaning formulation for cleaning hard surfaces, the improvement wherein the formulation contains a cleaning effective quantity of at least one methyl-end-capped alkyl or alkenyl polyglycol ether corresponding to formula (I):

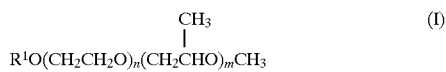

in which R¹ linear or branched alkyl or alkenyl group containing 6 to 22 carbon atoms, n is an average number of 4 to 15 and m is an average number of 0.5 to 1.5.

14. A methyl-end-capped alkyl or alkenyl polyglycol ether or a mixture of such ethers corresponding to formula (I):

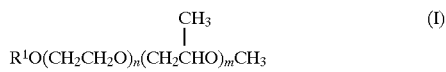

in which R¹ is a linear or branched alkyl or alkenyl group containing 6 to 22 carbon atoms, n is an average number of 4 to 15 and m is an average number of 0.5 to 1.5.

15. The ether or mixture of ethers of claim 14 wherein R¹ is an alkyl or alkenyl group containing 8 to 18 carbon atoms.

16. The ether or mixture of ethers of claim 14 wherein R¹ is an alkyl group containing 16 to 20 carbon atoms branched in the 2-position.

17. The ether or mixture of ethers of claim 14 wherein m is an average number of 1 to 1.2.

18. The ether or mixture of ethers of claim 14 wherein n is an average number of 4 to 12.

19. The ether or mixture of ethers of claim 17 wherein n is an average number of 4 to 12.

20. The formulation of claim 13 wherein in formula I, m is an average number of 1 to 1.2.

* * * * *